(12) United States Patent
El-Refaey

(10) Patent No.: US 8,148,337 B2
(45) Date of Patent: Apr. 3, 2012

(54) VAGINAL COMPOSITIONS FOR TREATING PELVIC TISSUE INFECTIONS AND TRAUMAS

(76) Inventor: Hazem El-Refaey, London (GB)

( * ) Notice: Subject to any disclaimer, the term of this patent is extended or adjusted under 35 U.S.C. 154(b) by 284 days.

(21) Appl. No.: 10/563,234

(22) PCT Filed: Jul. 2, 2004

(86) PCT No.: PCT/GB2004/002867
§ 371 (c)(1),
(2), (4) Date: Aug. 8, 2006

(87) PCT Pub. No.: WO2005/004880
PCT Pub. Date: Jan. 20, 2005

(65) Prior Publication Data
US 2007/0066545 A1    Mar. 22, 2007

(30) Foreign Application Priority Data

Jul. 4, 2003  (GB) .................................. 0315671.8

(51) Int. Cl.
*A61K 31/70*    (2006.01)
(52) U.S. Cl. ........................................................ 514/29
(58) Field of Classification Search .................... 514/29, 514/152
See application file for complete search history.

(56) References Cited

U.S. PATENT DOCUMENTS

| 4,160,827 A | 7/1979 | Cho et al. ........................ 424/199 |
| 4,496,587 A | 1/1985 | Renis et al. ..................... 514/573 |
| 4,997,823 A * | 3/1991 | Herschler ....................... 514/154 |
| 5,527,534 A | 6/1996 | Myhling ........................ 424/430 |
| 6,414,028 B1 | 7/2002 | Buyuktimkin et al. ........ 514/573 |
| 6,899,890 B2 * | 5/2005 | Kirschner et al. ............. 424/430 |
| 2002/0128313 A1 | 9/2002 | Schmitt et al. ................ 514/530 |
| 2003/0018049 A1 | 1/2003 | Godek et al. .................. 514/317 |

FOREIGN PATENT DOCUMENTS

| CN | 1186666 | 8/1998 |
| CN | 1242193 A | 1/2000 |
| CN | 1245059 | 2/2000 |
| GB | 2 293 101 A | 3/1996 |
| WO | WO 99/02145 | 1/1999 |
| WO | WO 02/072066 A1 | 9/2002 |
| WO | WO 02/087596 A3 | 11/2002 |
| WO | WO 02/092097 A1 | 11/2002 |
| WO | WO 03/039559 A1 | 5/2003 |
| WO | WO 03/079981 A2 | 10/2003 |

OTHER PUBLICATIONS

Article entitled *Bioavailability of Azithromycin*; MILNEK, 1995; 9th International Congress of Chemotherapy.

* cited by examiner

*Primary Examiner* — Elli Peselev
(74) *Attorney, Agent, or Firm* — Renner Kenner Greive Bobak Taylor & Weber

(57) ABSTRACT

A method of treatment for a pelvic tissue infection by vaginally administering an antibiotic and a prostaglandin to a patient is disclosed. A method of reducing surgical trauma resulting from a gynaecological operation by administering vaginally a composition comprising an antibiotic and a prostaglandin to a patient is also disclosed.

16 Claims, No Drawings

VAGINAL COMPOSITIONS FOR TREATING PELVIC TISSUE INFECTIONS AND TRAUMAS

The present invention relates to pharmaceutical compositions suitable for vaginal or rectal administration, kits of such pharmaceutical compositions and methods of medical treatment including the vaginal or rectal administration of pharmaceutical compositions.

Induction of abortion and uterine evacuation of a failed pregnancy is associated with significant morbidity. This is because of the associated complications like uterine perforation and infection.

Prostaglandin administered preoperatively softens the cervix and reduces the trauma. In the last decade misoprostol administered vaginally has become the prostaglandin agent of choice worldwide because of its stability at room temperature. It is one of the agents that Royal College of Obstetricians and Gynaecologists (RCOG) recommends for cervical priming preoperatively.

The RCOG also recommends that all women undergoing abortion should either be treated for infections such as chlamydial and/or anaerobes or they should be screened and treated for such infections.

Genital Chlamydial trachomatis infection is most common in the youngest sexually active population (16-19 year old women and 20-24 year old men). In 1999, UK genitourinary clinics reported around 57,000 new episodes of genital infections (around 33,000 in women and 24,000 in men). This infection usually co-exists with other sexually transmitted infections, particularly gonorrhoea. Treatment options include Doxycycline or Azithromycin, but the former is associated with poor patient compliance. The use of Azithromycin is applicable to treat both men and women.

Azithromycin is unique in that it is a tissue directed antibiotic. Unlike other groups of antibiotics taken by mouth, it is absorbed rapidly from the gut to the blood stream, into the tissues and the focus of infection. A recent meta-analysis of studies so far has shown that given as a single 1-gm dose orally, its efficacy to treat chlamydial infection and patient's tolerance is similar to that of a week-long course of Doxycycline. Though Azithromycin orally as a single dose is more appealing, 25% of women will experience side effects.

Azithromycin is licensed orally for the treatment of infections of the respiratory tract, skin and soft tissue. In gynaecology, it is licensed for uncomplicated genital infections due to chlamydia trachomatis. In 1980s, PLIVA and Pfizer were first granted patent protection in Belgium and thereafter worldwide for Azithromycin. It was first registered as Sumamed in 1988.

Despite the associated high efficacy, no attempts have been made to investigate other non-invasive routes of azithromycin administration. The only attempt to administer azithromycin rectally resulted in a negative study. The result being negative did not enable the group to publish this report. Based on their study they concluded that the bioavailability of azithromycin administered rectally was highly variable and low probably due to limited absorption. (George Melnik et al. Bioavailability of azitlhromnycin when delivered rectally. Presented at the 19$^{th}$ International congress of chemotherapy, Montreal, 1995.) This inconsistency in bioavailability meant that no other non-oral route was considered practical.

A solution to these problems has been sought.

According to a first aspect of the invention there is provided a pharmaceutical composition for use in the treatment and/or prevention of a pelvic tissue infection by vaginal administration which composition comprises an antibiotic and a pharmaceutically acceptable carrier or diluent.

According to a second aspect of the invention there is provided a pharmaceutical composition comprising, in admixture or separately:
(a) an antibiotic; and
(b) a prostaglandin.

The composition according to the second aspect of the invention is preferably for use by vaginal and/or rectal administration in reducing surgical trauma resulting from gynaecological operation.

According to the invention there is further provided a kit comprising
(a) an antibiotic,
(b) a prostaglandin and
(c) instructions for the simultaneous, sequential or separate administration of (a) and (b) to a patient in need thereof.

The kit is preferably for use by vaginal and/or rectal administration in reducing surgical trauma resulting from a gynaecological operation.

According to the invention there is also provided a use of the composition according to the first aspect of the invention in the manufacture of a medicament for use in the treatment and/or prevention of pelvic tissue infection by vaginal and/or rectal administration.

According to the invention there is also provided use of a composition according to the second aspect of the invention in the manufacture of a medicament for use by vaginal and/or rectal administration in reducing surgical trauma resulting from a gynaecological operation.

According to the invention there is provided use of a kit according to the invention in the manufacture of a medicament for use by vaginal and/or rectal administration in reducing surgical trauma resulting from a gynaecological operation.

According to the invention there is further provided use of an antibiotic in the manufacture of a kit according to the invention or of a composition according to the second aspect of the invention which kit or composition is for use by vaginal and/or rectal administration in reducing surgical trauma resulting from a gynaecological operation.

According to the invention there is further provided use of an antibiotic in the manufacture of a composition according to the first aspect of the invention for use in the treatment and/or prevention of a pelvic tissue infection by vaginal or rectal administration.

According to the invention there is also provided use of a prostaglandin in the manufacture of a kit according to the invention or of a composition according to the second aspect of the invention which kit or composition is for use by vaginal and/or rectal administration in reducing surgical trauma resulting from a gynaecological operation.

According to a third aspect of the invention there is provided a method of treating and/or preventing a pelvic tissue infection which method comprises administering vaginally or rectally a therapeutically effective amount of an antibiotic to a patient in need of such treatment.

According to a fourth aspect of the invention there is provided a method of reducing surgical trauma resulting from a gynaecological operation which method comprises administering vaginally or rectally a therapeutically effective amount of an antibiotic and of a prostaglandin to a patient in need of such treatment.

It has surprisingly been found that by administering an antibiotic vaginally, significant levels of absorption into pelvic tissues are achieved. These are the tissues required to treat chlamydial infections. As in the case of misoprostol, given to soften the cervix preoperatively, it is believed that altering the route of administration may enable the reduction of the side effects associated with the use of antibiotics.

This is important, as it is pertinent in two fields of public health:
1) Transcervical procedures especially induction of abortion and evacuation of uterus in failed pregnancy; and
2) Prevention of infection and in particular pelvic infection and may be more so in sexually transmitted infections.

In keeping with the RCOG guidelines, women need a cervical softening agent and an antibiotic to deal with possible undetected chlamydial infection. An advantage of the composition according to the second aspect of the invention is that it reduces these two interventions to one which will improve compliance and be more convenient for the patient.

The composition according to the first aspect of the invention optionally further comprises an analgesic, a non-steroidal antiinflammatory drug (NSAID), and/or a local anaesthetic drug. Examples of suitable analgesics include NSAIDs like diclofenac or agents like paracetamol. Examples of suitable local anaesthetic drugs include lignocaine, bupivacaine or ropivacaine.

The antibiotic used in the invention is preferably azithromycin, but may include combination with other antibiotics for example metronidazole. The prostaglandin is preferably misoprostol, but may include cervagem.

The amount of the antibiotic used in the invention is preferably from 250 milligrams to 1000 milligrams of azithromycin, more preferably from 500 to 1000 milligrams. The amount of the prostaglandin used in the invention is 50 micrograms to 1000 micrograms of misoprostol, more preferably from 100 to 800 micrograms.

The composition according to the second aspect of the invention preferably also includes a pharmaceutically acceptable carrier or diluent.

The compositions according to the invention are formulated to be suitable for vaginal and/or rectal administration. Each is optionally in the form of a tablet, pessary, suppository, cream, gel, bio-adhesive, slow release preparation and/or ointment. Examples of a pharmaceutically acceptable carrier or diluent for use in a composition according to the invention include cellulose, cellulose derivatives (such as hydroxy-propyl-methylcellulose), polyethylene glycol and a vegetable oil.

Where the compositions of the present invention are in the form of a suppository, the suppository can be prepared in a conventional manner using a conventional pharmaceutically acceptable carrier or diluent for the suppository.

The pharmaceutically acceptable carrier or diluent for such a suppository may include an oil and fat from animal and vegetable such as olive oil, corn oil, castor oil, cotton seed oil, oil from wheat with germ, cacao oil, beef tallow, pork tallow, wool tallow, turtle tallow, squalene or a hardened oil, an oil and fat from mineral such as Vaseline (trade mark), white soft paraffin, solid paraffin, liquid paraffin, dehydrated lanolin or silicon oil, a wax such as hohoba oil, carnauba wax, yellow bees wax or lanolin, or a partially synthetic or totally synthetic glycerin aliphatic acid ester such as mono, di or triglyceride of a middle or higher aliphatic acid such as a straight-chain saturated aliphatic acid (e.g. lauric acid, myristic acid, palmitic acid or stearic acid), or a straight-chain unsaturated aliphatic acid (e.g. oleic acid, linoleic acid or linolenic acid). The commercially available products are exemplified Witepsol [manufactured by Dynamitnobel Co.; a mixture of mono-, di- and tri-glycerides of $C_{12}$-$C_{18}$ saturated aliphatic acid, in more detail, Witepsol H series (e.g. Witepsol H5, H12, H19, H32, H35, H37, H39, H42, H175 or H185), Witepsol W series (e.g. Witepsol W25, W31, W35 or W45), Witepsol E series (e.g. Witepsol E75, E76, E79 or E85) or Witepsol S series (e.g. Witepsol S52, S55 or S58) are included]; Pharmasol (manufactured by Nippon Oils and Fats Co.); Isocacao (manufactured by Kao Co.); SB (manufactured by Kanegafuchi Chemical Co. and Taiyo Yusi Co.; a mixture of mono-, di- and tri-glycerides of $C_{12}$-$C_{18}$ saturated aliphatic acid, in more detail, SB-H, SB-E or SB-AM are included); Nopata (manufactured by Henkel AG.); Sapoyer (manufactured by Gattfords Co.; a mixture of mono-, di- and tri-glycerides of $C_{10}$-$C_{18}$ saturated aliphatic acid, in more detail, Sapoyer NA, Sapoyer OS, Sapoyer AS, Sapoyer BS, Sapoyer BM or sapoyer DM are included); Masaesthalinum (manufactured by Dynamitnobel Co.; a mixture of mono-, di- and tri-glyceride of $C_{10}$-$C_{18}$ saturated aliphatic acid, in more detail, Masaestlialinum A, AB, B, BB, BC, BCF, C, D, E or BD and Masaasthalinum 299 are included); or Migriol 810 or Migriol 812 (manufactured by Dynamitnobel Co.; a mixture of triglycerides of $C_8$-$C_{12}$ saturated aliphatic acid, in more detail, one or more of them may optionally be incorporated when the partially synthetic or totally synthetic glycerin aliphatic acid ester as mentioned above are incorporated). Further, other synthetic products such as polyethylene glycol or polyoxyethylene alcohol can be exemplified.

To the suppository may be added, if necessary, a preservative, a stabilizer, a surfactant, an aromatic, a pH adjustor or a purified water.

The suppository may be in various forms such as a rectal suppository which is solid at the normal temperature and melts at a body temperature; an ointment or liquid enema which can be prepared by dissolving or suspending the compound of the present invention in a liquid base; a soft capsule for the rectal administration; or an injection for the rectal administration.

The compositions and kit according to the invention are preferably for use via the vaginal route of administration. Similarly the methods of the invention preferably involve vaginal administration.

The invention can be used to treat infection of pelvic tissues. Pelvic tissues include the cervix, endometrium, fallopian tubes and parametrium. Infections, which can be treated by the invention, include sexually transmitted infections like chlamydia, gonorrhoea and trichomonas vaginalis.

The composition according to the second aspect of the invention and the kit according to the invention are preferably for use by vaginal and/or rectal administration to a patient about to undergo a genitourinary tract or lower bowel surgical operation. Similarly the method according to the fourth aspect of the invention preferably comprises administering the treatment to a patient about to undergo a gynaecological operation. Examples of such operations include surgical and medical abortion, uterine evacuation of a failed pregnancy and transcervical operations undertaken outside pregnancy.

The antibiotic and prostaglandin of the kit of the invention can be administered simultaneously, sequentially or separately to reduce surgical trauma resulting from a gynaecological operation. By sequential is meant that the active ingredients (which are the antibiotic and prostaglandin) are administered one after the other. The desired effect is still achieved if they are administered separately but preferably less than about 12 hours apart, more preferably less than about 2 hours apart, most preferably less than about 30 minutes apart.

The invention may optionally be used to treat a human or animal patient, especially a human or mammal patient.

In the kit according to the invention, the antibiotic and the prostaglandin are preferably provided in the form of pharmaceutically acceptable compositions either the antibiotic or the prostaglandin in association with a pharmaceutically acceptable carrier or diluent.

Examples of suitable formulations include a pessary comprising azithromycin 1000 mg with a carrier such as polyethylene glycol or witepsol; a suppository formulation of azithromycin 1000 mg with a carrier such as polyethylene glycol or cocoa butter or witepsol; a pessary formulation of a prostaglandin (for use in the kit according to the invention) comprising misoprostot 800 microgram with a carrier such as hydroxypropyl methyl cellulose or witepsol or a free fatty acid, hard fat base; a suppository formulation of a prostglandin (for use in the kit according to the invention) comprising misoprostol 800 microgram with a carrier such as hydroxypropyl methyl cellulose or polyethylene glycol or witepsol; a pessary formulation of a prostaglandin and an antibiotic comprising misoprostol 800 microgram and azithromycin 1000 mg with a carrier such as witepsol or polyethylene glycol; a suppository formulation of a prostaglandin and an antibiotic comprising a misoprostol 800 microgram and azithromycin 1000 mg with hydroxypropyl methyl cellulose or witepsol. The procedure for the preparation of such a formulation would be well known to a person of skill in the art, particularly on the basis of the disclosure in Example 1.

The invention is illustrated by the following examples, which are not intended to limit the scope of the application.

EXAMPLE 1

Example of a pessary formulation of azithromycin 500 mg and misoprostol 400 mcg:

TABLE 1

| Ingredient | Amount |
|---|---|
| AZITHROMYCIN powder | 50.00 g |
| MISOPROSTOL 200 mcg Tablets | 200 |
| WITEPSOL S55 | 209.00 g |

A pessary formulation was prepared using the ingredients set out in Table 1. The misoprostol tablets were crushed using a blender. The resulting powder was placed in a mortar and triturated with the azithromycin. Once well mixed, the molten witepsol was added and stirred well. The mixture was then poured into one hundred 3 g moulds and allowed to set.

Pilot Study I

This study was done in pre-menopausal women undergoing hysterectomy for benign causes. Ten patients were given azithromycin tablets (Zithromax, Pfizer) orally or vaginally at least 18 hours preoperatively and then tissue biopsies were taken from hysterectomy samples. The endometrial, cervical and fallopian tube levels of azithromycin were then measured using tissue pharmacokinetics using agar well diffusion bioassay method with micrococcus luteus ATCC 9341 as indicator organism, an appropriate method for this tissue directed antibiotic. (Girard A E et al. 1987. *Pharmacokinetics and in-vivo studies with azithromycin (CP-62.993), a new macrolide with extended half-life and excellent tissue distribution. Antimicrobial Agents and chemotherapy.* 31: 1948-54.) Previous work has defined azithromycin levels greater than 2.0 mg/kg tissue as significant.

Table 2 shows for each patient the route of administration and the time after dosage at which the serum and tissue samples were taken. The azithromycin concentrations are given for the serum samples and for the endometrial, cervical and fallopian tube tissue samples.

TABLE 2

| | | | Serum | Tissue concentration (mg/kg) | | |
|---|---|---|---|---|---|---|
| Admin. No | Route | Sample time (hrs) | conc. (mg/l) | Endometrium | Cervix | Fallopian tubes |
| 1 | Oral | 20.2 | — | 3.5 | 12.0 | 13.7 |
| 2 | Oral | 22.9 | 0.1 | 11.3 | no sample | 7.4 |
| 3 | Vaginal | 21.2 | NDL | 3.6 | 3.5 | 1.9 |
| 4 | Oral | 24.9 | 0.04 | 11.2 | 4.7 | 4.9 |
| 5 | Vaginal | 20.3 | NDL | 6.4 | 4.2 | 5.5 |
| 6 | Vaginal | 24.7 | NDL | NDL | 0.7 | 0.2 |
| 7 | Vaginal | 24.0 | 0.05 | 46.8 | 15.7 | 31.8 |
| 8 | Oral | 19.5 | 0.1 | 15.9 | 17.0 | 27.6 |
| 9 | Vaginal | 26.7 | 3.1 | 15.8 | 11.9 | 7.7 |
| 10 | Oral | 21.9 | 0.1 | 10.6 | 8.7 | 5.7 |

NDL = No detectable level

Patient no. 6 was not compliant with treatment. No tablets (intact or partly dissolved) were found in the vagina. She discharged herself against medical advice on day 2 post hysterectomy.

The data in Table 2 shows that administering azithromycin vaginally surprisingly results in significant levels of the antibiotic being present in pelvic tissues even 24 hours after treatment.

It is to be noted that Zithromax is formulated for oral administration and therefore it is expected that use of a composition according to the first aspect of the invention formulated for vaginal administration will give improved results.

Pilot Study II

This study was done on 13 women undergoing surgical pregnancy termination. A special formulation as previously described of Azithromycin and Misoprostol was developed in a pessary format. The pessaries were administered 2-4 hours before surgical termination of the pregnancy. Biopsies were obtained from the cervix and endometrium. In addition blood levels were studied. The results are shown in Table 3.

TABLE 3

| Pt No | Rx time | Blood time | Biopsy time | Time after dose (hours) | Serum conc (mg/l) | Tissue conc(mg/kg) Cervix | Tissue conc(mg/kg) Endometrium |
|---|---|---|---|---|---|---|---|
| 1 | 12.00 | 15.00 | 15.35 | 3.6 | NDL | 820.5 | 8.3 |
| 2 | 12.30 | 15.45 | 15.50 | 3.7 | NDL | 122.8 | NST |
| 3 | 11.50 | 14.25 | 14.30 | 2.7 | NDL | 2554.1 | 23.7 |
| 4 | 12.00 | 14.55 | 15.00 | 3.0 | NDL | 864.9 | NST |
| 5 | 11.55 | 15.30 | 15.35 | 3.7 | NDL | 1190.3 | 2.9 |
| 6 | 12.05 | 15.50 | 15.55 | 3.8 | NDL | 714.3 | NST |
| 7 | 11.15 | 14.05 | 14.15 | 3.0 | NDL | 257.9 | NST |
| 8 | 11.15 | 14.25 | 14.35 | 3.3 | NDL | 618.5 | NST |

TABLE 3-continued

| Pt No | Rx time | Blood time | Biopsy time | Time after dose (hours) | Serum conc (mg/l) | Tissue conc(mg/kg) Cervix | Tissue conc(mg/kg) Endometrium |
|---|---|---|---|---|---|---|---|
| 9  | 11.25 | 14.40 | 14.55 | 3.5 | NDL  | 629.7  | NST |
| 10 | 11.40 | 15.05 | 15.20 | 3.7 | NDL  | 1071.7 | NST |
| 11 | 12.00 | 15.30 | 15.40 | 3.7 | 0.07 | 968.7  | NST |
| 12 | 11.15 | 14.30 | 14.40 | 3.4 | NDL  | 8.3    | NST |
| 13 | 11.20 | 15.25 | 15.30 | 4.2 | NDL  | 466.7  | NST |

NDL = No detectable level
NST = No sample taken

These results clearly show the very high level of azithromycin in the tissues compared to the data in table II

The invention claimed is:

1. A method of treating a pelvic tissue infection which method comprises administering vaginally a therapeutically effective amount of an antibiotic and of a prostaglandin to a patient in need of such treatment wherein the antibiotic includes 500 milligrams of azithromycin and wherein the prostaglandin includes 400 micrograms of misoprostol.

2. A method as defined in claim 1 wherein the infection is a sexually transmitted disease.

3. A method as defined in claim 1 wherein the antibiotic further includes metronidazole.

4. A method as defined in claim 1, wherein the infected tissue is a cervix, endometrium, fallopian tube or parametrium.

5. A method of reducing surgical trauma resulting from a gynaecological operation which method comprises administering vaginally a composition comprising a therapeutically effective amount of an antibiotic and of a prostaglandin to a patient in need of such treatment wherein the antibiotic includes 500 milligrams of azithromycin and wherein the prostaglandin includes 400 micrograms of misoprostol.

6. A method as defined in claim 5 which comprises administering the composition to a patient about to undergo a gynaecological operation.

7. A method as defined in claim 6 wherein the operation includes a surgical or medical abortion, uterine evacuation of a failed pregnancy or a transcervical operation undertaken outside pregnancy.

8. A method as defined in claim 5 wherein the composition comprises a pharmaceutically acceptable carrier or diluent.

9. A method as defined in claim 5 wherein the prostaglandin further includes cervagem with the misoprostol.

10. A method as defined in claim 5 wherein the antibiotic further includes metronidazole.

11. A method as defined in claim 5 wherein the patient is a human or animal patient, especially a human or mammal patient.

12. A method as defined in claim 1 wherein the prostaglandin further includes cervagem with the misoprostol.

13. A method according to claim 1 wherein the composition is provided in the form of a two part kit wherein the first part (a) comprises azithromycin and a pharmaceutically acceptable carrier or diluent and wherein the second part (b) comprises misoprostol, optionally with cervagem.

14. A method according to claim 13 wherein parts (a) and (b) are administered simultaneously, sequentially or separately.

15. A method according to claim 13 wherein part (b) of the kit comprises a pharmaceutically acceptable carrier or diluent.

16. A method according to claim 1 wherein the treatment is for reducing surgical trauma resulting from a gynaecological operation.

* * * * *